United States Patent [19]

Boesten et al.

[11] Patent Number: 5,276,190

[45] Date of Patent: Jan. 4, 1994

[54] METHOD FOR THE PREPARATION OF AN ALCOHOL

[75] Inventors: Wilhelmus H. J. Boesten, Sittard; Harold M. Moody, Maastricht; Quirinus B. Broxterman, Sittard, all of Netherlands

[73] Assignee: DSM N.V., Heerlen, Netherlands

[21] Appl. No.: 950,713

[22] Filed: Sep. 25, 1992

[30] Foreign Application Priority Data

Sep. 26, 1991 [NL] Netherlands .................. 9101623

[51] Int. Cl.$^5$ ........................................... C07C 209/68
[52] U.S. Cl. ......................... 564/340; 544/335; 548/205; 548/235; 548/340.1; 548/507; 564/355; 564/356; 564/488; 564/503
[58] Field of Search ............... 564/340, 355, 356, 488, 564/503; 544/335; 548/205, 235, 340.1, 507

[56] References Cited

U.S. PATENT DOCUMENTS 2,618,658 6/1949 Caldwell .............................. 260/584
4,994,017 2/1991 Aubard et al. ...................... 564/355

OTHER PUBLICATIONS

Journal of Organic Chemistry, vol. 48, No. 11, Jun. 3, 1983, Easton US, pp. 1916–1919.
Houben–Weyl "Methoden der Organischen Chemie", 1957, vol. XI/1, pp. 595–597.

*Primary Examiner*—Richard L. Raymond
*Attorney, Agent, or Firm*—Cushman, Darby & Cushman

[57] ABSTRACT

The invention relates to a method for the preparation of an α,α-disubstituted α-amino alcohol from the corresponding amide with the aid of sodium in the presence of an alcohol as solvent. The conversion of amino acid amide to amino alcohol proceeds virtually quantitatively. Moreover, the reduction of the amino acid amide to the corresponding amino alcohol proceeds with retention of optical activity.

5 Claims, No Drawings

METHOD FOR THE PREPARATION OF AN ALCOHOL

The invention relates to a method for the preparation of an α,α-disubstituted-α-amino alcohol from the corresponding amide with the aid of sodium in an alcoholic solution.

A known preparation of these optically active 2,2-disubstituted 2-amino alcohols is the reduction of the corresponding amino acids with borane, $(BH_3)_2$, or lithium aluminium hydride, $LiAlH_4$. Because these reducing agents are very expensive, this reduction is not used on a large scale. The method according to the invention has the advantage that, in contrast to the reduction of amino acids with borane or lithium aluminium hydride, the alcohols can now be prepared on an industrial scale.

It has been found that with the process according to the invention in an economically attractive process a yield of the corresponding alcohol can be obtained, which is as a rule between 95 and 100%. Moreover, the reduction of optically active α,α-disubstituted o-amino acid amides proceeds with retention of optical activity.

A reduction of amides to alcohols in general is disclosed in "Methoden der organischen Chemie"["Methods of organic chemistry"] (Houben-Weyl), Georg Thieme Verlag Stuttgart (1957), volume XI/1, pp. 595-597, in which the reduction of amides with sodium in amyl alcohol in the complete absence of water is discussed. However, the reduction is found to proceed in two directions; in addition to the alcohol main product, appreciable amounts of amine are also formed. With this procedure saponification of the amide occurs to a varying degree under the influence of water.

Two other methods for the conversion of an amide with sodium into the corresponding alcohol are described in J. Org. Chem. 1983, 48, 1916-1919, liquid ammonia being used as the solvent. In this reference a carboxylamide group, which may or may not form part of the o-amino acid fragment of an α-H-α-amino acid, is converted into an alcohol group. The yields of 2-H-2-amino alcohol which are obtained here range from 20 to 85%. If these yields are taken into account, it must be regarded as surprising that it is precisely α,α-disubstituted α-amino acid amides which can be virtually quantitatively converted to the corresponding alcohol when use is made of the method according to the invention.

In the two methods described in the last-mentioned reference use is made of reaction mixtures which have a substrate concentration lower than that in the method according to the invention. The examples in the reference give a concentration of 0.1-1 per cent by weight of amide. The two methods described in the said reference also have the disadvantage that they use a lot more sodium; 10-20 equivalents compared with the 4-8 equivalents used in the method according to the invention. The concentration of the amide which is reduced is also much lower. The method according to the invention thus gives a higher yield of alcohol at a higher substrate concentration and using a smaller amount of sodium. The method according to the invention is also easier to use on a commercial scale than the known methods.

The first method from the above-mentioned reference, method A, describes the successive treatment of the amide with liquid ammonia and $NH_4Cl$. If this treatment is repeated eleven times a yield of up to 84.2% of the corresponding alcohol can be obtained. Method A is thus more time-consuming than the method according to the invention. An additional factor is that the yield from method A is lower.

The second method, method B, describes the reduction of an amide to the corresponding alcohol in the presence of sodium and liquid ammonia in the presence of a proton-donating component, for example methanol. An alcohol yield of up to 79.3% can be achieved in the case of this treatment.

In the method according to the invention, the corresponding 2,2-disubstituted 2-amino alcohol is prepared using α,α-disubstituted α-amino acid amide as the starting material. The substituents can be identical or different and comprise aromatic and aliphatic hydrocarbons, such as alkyl, alkenyl, cycloalkyl, aryl, aralkyl and alkaryl groups, it also being possible for these substituents to contain hetero-atoms such as sulphur, oxygen and nitrogen atoms and it also being possible for the substituents to be substituted by, for example, halogens. The substituents will usually contain 1-20 carbon atoms. Examples of suitable substituents are: methyl, ethyl, n-propyl, isopropyl, n-butyl, sec-butyl, isobutyl, tert-butyl, phenyl, benzyl, 2-phenethyl, 4-methoxyphenyl, 3,4-dimethoxybenzyl, 4-methoxybenzyl, 3-aminopropyl, 4-aminobutyl, 2-methylmercaptoethyl, 3-methylmercaptopropyl, methylmercaptomethyl, allyl, methallyl, crotyl, cinnamyl, imidazolylmethyl, indolylmethyl, thienyl(methyl), furyl(methyl), pyridinyl(methyl), oxazolyl(methyl), thiazolyl(methyl) and pyrimidinyl(methyl).

The starting compound, the α,α-disubstituted α-amino acid amide, can be obtained, for example, by partially hydrolysing the corresponding aminonitrile—obtained by reaction of the corresponding ketone with hydrocyanic acid and ammonia—with a strong acid to give the amide. Another method is the conversion of the corresponding amino acid, which may or may not be optically active, with the aid of phosgene to give the corresponding N-carboxyanhydride, followed by treatment of the anhydride with ammonia. The R-enantiomer of α,α-disubstituted α-amino acid amides can be prepared from the racemic mixture, as described in EP-A-0179523, by means of stereoselective enzymatic hydrolysis with the microorganism Mycobacterium neoaurum.

The solvent used is as a rule an alcohol. Examples of suitable alcohols are lower aliphatic alcohols containing 1-7 carbon atoms, such as methanol, ethanol and propanol. Propan-1-ol is preferably used. The concentration of the α,α-disubstituted o-amino acid amide is chosen as high as possible and is mainly determined by the solubility of the amide. Usually the concentration corresponds to 2-25% by weight of amino acid amide calculated with respect to the total amount of amino acid amide and solvent. Preferably, 5-15% by weight of amino acid amide are used.

The amount of sodium which is used in the reaction according to the invention can vary within wide limits; the theoretically calculated minimum amount of sodium which is needed for 100% conversion of the amide to the corresponding alcohol is 4 equivalents per mol of amide. The amount of sodium which is used in practice is usually 4-8, preferably 5-6, equivalents of sodium per mol of amide.

The reaction mixture usually reacts for 1-10 hours, preferably for 2-4 hours, with heating at a temperature of 20°–140° C., preferably at the reflux temperature. The α,α-disubstituted α-amino acid amide is virtually quantitatively converted to the corresponding alcohol in this reaction.

The reaction mixture can be further worked up in a manner known per se. One method for this is that the reaction mixture is quenched with water and the product is isolated by means of extraction with chloroform. Another method, described in European Patent EP-0322982, proceeds by first converting the 2,2-disubstituted 2-amino alcohol in an aqueous medium to give a Schiff's base, extracting the latter from the aqueous phase and then hydrolysing it with acid, the 2,2-disubstituted 2-amino alcohol precipitating in the form of a salt.

According to one suitable embodiment of the method according to the invention, the starting compound, the α,α-disubstituted α–amino acid amide, is dissolved in propan-1-ol, the concentration of the α,α-disubstituted α-amide being approximately 4 per cent by weight. 5–6 equivalents of sodium per mol of amide are then added and the reaction mixture reacts for 2 hours at the reflux temperature.

The method according to the invention has the additional advantage that complete removal of water prior to the reaction is not necessary, with the result that the present invention is easily applicable on a large scale. Even the presence of a few per cent of water in the reaction mixture does not have an adverse influence on the reaction.

The 2,2-disubstituted 2-amino alcohols formed can be used in various ways. Applications which can be considered are use as a racemate-free cleavage agent, use as an optically active ligand in catalytic asymmetric syntheses and use as an optically active synthetic intermediate in pharmaceutical application.

The invention is further illustrated by the following examples without, however, any limitation being implied.

EXAMPLE I

Synthesis of D-α-methyl-homophenylalaninol 4.0 grams of D-α-methyl-homophenylalaninamide were dissolved in 50 ml of propan-1-ol. The solution was heated to reflux, after which 3.3 g (7.0 equivalents) of sodium were added in pieces over a period of 30 minutes, an exothermic reaction taking place with evolution of gas. The mixture was refluxed for a further 2 hours. After cooling to room temperature, 20 ml of water were added carefully and the liquid was distilled off under vacuum (about 50° C., 16 mm Hg). 30 ml of water were then added and the mixture was extracted with chloroform (3×30 ml). Concentration of the chloroform phase yielded 3.7 g (99%) of white D-α-methyl-homophenylalaninol crystals. With the aid of 400 MHz $^1$H NMR, an enantiomeric excess (e.e.) of >98% was found. In this procedure trifluoroanthrylethanol (TFAE) was used as shift reagent and D,L-α-methyl-homophenylalaninol, prepared in the same way, as reference material.

EXAMPLE II

Synthesis of D,L-α-ethyl-phenylglycinol

Reaction and working-up were carried out as described in Example I, using 4.0 grams of D,L-α-ethyl-phenylglycinamide in 50 ml of propan-1-ol and using 3.1 g (6.0 equivalents) of sodium. Yield: 3.6 g (98%) of white D,L-α-ethyl-phenylglycinol crystals.

αEXAMPLE III

Synthesis of D,L-α-allylphenylglycinol

Reaction and working-up were carried out as described in Example I, using 4.0 grams of D,L-α-allyl-phenylglycinamide in 50 ml of propan-1-ol and using 3.9 g (8.0 equivalents) of sodium. Yield: 3.7 g (99%) of white D,L-α-allylphenylglycinol crystals.

EXAMPLE IV

Synthesis of D,L-α-benzylmethioninol 1.5 g (8.0 equivalents) of sodium were added in pieces to a solution of 2.0 g of D,L-α-benzylmethioninamide in 24 ml of propan-1-ol and 1 ml of water under reflux. The mixture was then refluxed for a further 2 hours, cooled to room temperature and worked up as described in Example I. Yield: 1.9 g (100%) of D,L-α-benzylmethioninol in the form of a colourless oil.

EXAMPLE V

Synthesis of D,L-α-methylvalinol

The reaction was carried out as described in Example I using 4.0 g of D,L-α-methylvalinamide in 50 ml of propan-1-ol, using 4.2 g (6.0 equivalents) of sodium. The product was obtained (as described in European Patent EP-0322982) by converting it to a Schiff's base (using 1.1 equivalent of benzaldehyde at pH 11), extracting the latter from the aqueous phase and hydrolysing it with hydrochloric acid and isolating the product in the form of the HCl salt. Yield: 4.5 g (95%) of D,L-α-methylvalinol in the form of a white crystalline substance.

We claim:

1. Method for the preparation of an α,α-disubstituted-α-amino alcohol from the corresponding amide with the aid of sodium in the presence of an alcohol as solvent, wherein the reaction takes place at a temperature of between 20° and 140° C.

2. Method according to claim 1, characterised in that the solvent used in propan-1-ol.

3. Method according to claim 1, characterised in that the concentration of the α,α-disubstituted α-amino acid amide with respect to the total amount of α,α-disubstituted α-amino acid amide and solvent is 5–15 per cent by weight.

4. Method according to claim 1, characterised in that the amount of sodium corresponds to 5–6 equivalents per mol of α,α-disubstituted α-amino acid amide.

5. Method according to claim 1, characterised in that the reaction takes place at the reflux temperature.

* * * * *